(12) United States Patent
Goncharov et al.

(10) Patent No.: US 10,217,237 B1
(45) Date of Patent: Feb. 26, 2019

(54) SYSTEMS AND METHODS FOR FORMING A DESIRED BEND ANGLE IN AN ORTHODONTIC APPLIANCE

(71) Applicant: ADITON LTD., Lamaca (CY)

(72) Inventors: Anton Olegovich Goncharov, Moscow (RU); Khamzat Saidovich Asabaev, Moscow (RU); Islam Khasanovich Raslambekov, Moscow (RU)

(73) Assignee: 3D MED AG, Zug (CH)

( * ) Notice: Subject to any disclaimer, the term of this patent is extended or adjusted under 35 U.S.C. 154(b) by 0 days.

(21) Appl. No.: 16/014,253

(22) Filed: Jun. 21, 2018

(51) Int. Cl.
*G06T 7/62* (2017.01)
*A61C 7/20* (2006.01)
*A61C 7/00* (2006.01)
*G06T 7/00* (2017.01)
*B21F 45/00* (2006.01)

(52) U.S. Cl.
CPC .............. G06T 7/62 (2017.01); A61C 7/002 (2013.01); A61C 7/20 (2013.01); B21F 45/008 (2013.01); G06T 7/0016 (2013.01); *A61C 2201/007* (2013.01); *G06T 2207/10016* (2013.01); *G06T 2207/20081* (2013.01); *G06T 2207/30036* (2013.01)

(58) Field of Classification Search
CPC combination set(s) only.
See application file for complete search history.

(56) References Cited

U.S. PATENT DOCUMENTS

| | | | |
|---|---|---|---|
| 5,431,562 A | 7/1995 | Andreiko et al. | |
| 5,447,432 A | 9/1995 | Andreiko et al. | |
| 5,966,682 A | 10/1999 | Gramckow et al. | |
| 6,250,918 B1 | 6/2001 | Sachdeva et al. | |
| 6,315,553 B1 | 11/2001 | Sachdeva et al. | |

(Continued)

FOREIGN PATENT DOCUMENTS

| | | |
|---|---|---|
| CN | 102113916 A | 7/2011 |
| CN | 203898469 U | 10/2014 |

(Continued)

OTHER PUBLICATIONS

English Abstract of CN203898469U retrieved on Espacenet on Jun. 19, 2018.

(Continued)

*Primary Examiner* — Anand P Bhatnagar
(74) *Attorney, Agent, or Firm* — BCF LLP

(57) ABSTRACT

A method for forming a desired bend angle in an orthodontic appliance comprising: obtaining desired bend angle; determining initial bend angle to be applied in gripped state; causing forming of a bend with initial bend angle; monitoring bending; in response to initial bend angle in the appliance in the gripped state being reached, causing the release of at least a portion of the appliance so that appliance is in the free state, measuring resultant angle of the bend in free state; selectively executing: in response to resultant angle being within a predefined tolerance of the desired bend angle, determining that desired bend angle has been reached; and in response to the resultant angle being outside the predefined tolerance level of the desired bend angle, iteratively applying an adjusted bend angle to the appliance in the gripped state until the desired bend angle is achieved as determined in the free state.

19 Claims, 7 Drawing Sheets

(56) References Cited

U.S. PATENT DOCUMENTS

| | | |
|---|---|---|
| 6,318,995 B1 | 11/2001 | Sachdeva et al. |
| 6,612,143 B1 | 9/2003 | Butscher et al. |
| 6,648,640 B2 | 11/2003 | Rubbert et al. |
| 6,732,558 B2 | 5/2004 | Butscher et al. |
| 6,755,064 B2 * | 6/2004 | Butscher ............ A61C 7/04 72/21.4 |
| 6,851,949 B1 | 2/2005 | Sachdeva et al. |
| 6,860,132 B2 * | 3/2005 | Butscher ............ A61C 7/04 72/302 |
| 6,928,733 B2 | 8/2005 | Rubbert et al. |
| 7,010,150 B1 | 3/2006 | Pfeiffer et al. |
| 7,076,980 B2 * | 7/2006 | Butscher ............ A61C 7/04 72/21.4 |
| 7,134,874 B2 * | 11/2006 | Chishti ............ A61C 7/00 433/24 |
| 7,283,891 B2 | 10/2007 | Butscher et al. |
| 7,310,446 B2 | 12/2007 | Kato et al. |
| 9,107,722 B2 | 8/2015 | Matov et al. |
| 9,901,705 B2 | 2/2018 | Armour et al. |
| 10,045,834 B2 * | 8/2018 | Gualano ............ A61C 7/143 |
| 2001/0002310 A1 * | 5/2001 | Chishti ............ A61C 7/00 433/24 |
| 2002/0025503 A1 | 2/2002 | Chapoulaud et al. |
| 2002/0180760 A1 | 12/2002 | Rubbert et al. |
| 2003/0056561 A1 * | 3/2003 | Butscher ............ A61C 7/04 72/295 |
| 2003/0070468 A1 * | 4/2003 | Butscher ............ A61C 7/04 72/295 |
| 2003/0194677 A1 | 10/2003 | Sachdeva et al. |
| 2003/0235803 A1 | 12/2003 | Nikolskiy |
| 2004/0073417 A1 | 4/2004 | Rubbert et al. |
| 2004/0110110 A1 * | 6/2004 | Chishti ............ A61C 7/00 433/24 |
| 2004/0175669 A1 | 9/2004 | Abels |
| 2004/0176866 A1 | 9/2004 | Abels et al. |
| 2004/0197727 A1 | 10/2004 | Sachdeva |
| 2004/0214129 A1 | 10/2004 | Sachdeva |
| 2005/0064360 A1 | 3/2005 | Wen |
| 2005/0070782 A1 | 3/2005 | Brodkin |
| 2005/0074716 A1 | 4/2005 | Cleary et al. |
| 2005/0089214 A1 | 4/2005 | Rubbert et al. |
| 2005/0130095 A1 | 6/2005 | Raby et al. |
| 2005/0170309 A1 | 8/2005 | Raby et al. |
| 2006/0078842 A1 | 4/2006 | Sachdeva et al. |
| 2006/0107720 A1 * | 5/2006 | Rubbert ............ A61C 7/02 72/307 |
| 2006/0127853 A1 | 6/2006 | Wen |
| 2006/0147872 A1 | 7/2006 | Andreiko |
| 2006/0210951 A1 | 9/2006 | Levanoni et al. |
| 2006/0240374 A1 | 10/2006 | Wen |
| 2006/0257815 A1 | 11/2006 | De Dominicis |
| 2007/0054231 A1 | 3/2007 | Manemann et al. |
| 2008/0141534 A1 | 6/2008 | Hilliard |
| 2008/0153053 A1 * | 6/2008 | Butscher ............ A61C 7/04 433/20 |
| 2008/0154644 A1 | 6/2008 | Butscher et al. |
| 2008/0220395 A1 | 9/2008 | Marshall et al. |
| 2009/0199609 A1 * | 8/2009 | Butscher ............ A61K 31/198 72/21.4 |
| 2009/0291417 A1 * | 11/2009 | Rubbert ............ A61C 7/00 433/215 |
| 2010/0114538 A1 | 5/2010 | Sporbert et al. |
| 2010/0223034 A1 | 9/2010 | Imgrund et al. |
| 2010/0275668 A1 * | 11/2010 | Riemeier ............ A61C 7/20 72/293 |
| 2011/0086322 A1 | 4/2011 | Baron et al. |
| 2011/0097682 A1 | 4/2011 | Curiel et al. |
| 2011/0104630 A1 | 5/2011 | Matov et al. |
| 2011/0191075 A1 | 8/2011 | Hultgren et al. |
| 2011/0314891 A1 | 12/2011 | Gilbert |
| 2012/0123576 A1 | 5/2012 | Pettersson et al. |
| 2014/0076015 A1 * | 3/2014 | Riemeier ............ B21F 1/008 72/37 |
| 2014/0360999 A1 | 12/2014 | Chun et al. |
| 2016/0114378 A1 | 4/2016 | Riemeier et al. |
| 2016/0317250 A1 | 11/2016 | Sachdeva et al. |

FOREIGN PATENT DOCUMENTS

| | | |
|---|---|---|
| CN | 105033105 A | 11/2015 |
| CN | 105618631 A | 6/2016 |
| EP | 2258303 A1 | 12/2010 |
| EP | 1301140 B2 | 7/2017 |
| KR | 101629136 B1 | 6/2016 |
| MX | 2013003893 A | 12/2013 |
| WO | 1999/014641 A1 | 3/1999 |
| WO | 2006100700 A1 | 9/2006 |
| WO | 2009056776 A2 | 5/2009 |
| WO | 2010/069121 A1 | 6/2010 |

OTHER PUBLICATIONS

English Abstract of CN105033105A retrieved on Espacenet on Jun. 19, 2018.
English Abstract of CN105618631A retrieved on Espacenet on Jun. 19, 2018.
English Abstract of KR101629136B1 retrieved on Espacenet on Jun. 19, 2018.
English Abstract of MX2013003893A retrieved on Espacenet on Jun. 19, 2018.
English Abstract of CN102113916 (A) retrieved on Espacenet on Jun. 19, 2018.
The partial European search report issued in respect of the EP application 18179183.1 dated Dec. 17, 2018.

* cited by examiner

SYSTEMS AND METHODS FOR FORMING A DESIRED BEND ANGLE IN AN ORTHODONTIC APPLIANCE

FIELD

The present technology relates to systems and methods for forming a desired bend in an orthodontic appliance.

BACKGROUND

In orthodontics, treatments for achieving alignment of malposed teeth in a patient include applying orthodontic appliances to the patient's teeth, such as pre-shaped orthodontic wire attached to the brackets which are themselves attached to the teeth. The wires are typically made from shape memory alloys which have the ability to recover their shape after being deformed. This re-shaping occurs at a predetermined temperature, usually around 38° C. Shape memory alloys used in orthodontic archwires include nickel-titanium alloys (e.g. Nitinol™), beta-titanium alloys, and copper nickel-titanium alloys.

The wires are typically pre-shaped into a desired shape by forming bends at desired positions and with desired angles, heating under tension, and super-cooling. The heating step typically comprises electric heating. Once pre-shaped, the wire is attached to the brackets by bending its shape to conform to the general shape of the malposed teeth. When the wire warms to mouth temperature it reverts to its original shape thereby exerting a force on the teeth to which it is attached to move them.

At least the bending portion of the pre-shaping process can be achieved manually or using bending apparatus such as those described in U.S. Pat. No. 6,612,143, U.S. Pat. No. 6,732,558, U.S. Pat. No. 6,755,064, U.S. Pat. No. 6,860,132, U.S. Pat. No. 7,076,980, U.S. Pat. No. 7,283,891 and US2010275668.

In certain pre-shaping methods, the desired bend in the orthodontic appliance is achieved by iteratively bending the orthodontic appliance, and assessing the acquired bend until the desired bend is achieved. This can take many iterations which has associated inconveniences of material property degradation in the orthodontic appliance, as well as increased time and cost per orthodontic appliance manufacture.

U.S. Pat. No. 6,612,143 describes a robotic bending apparatus for bending archwires and other types of elongate, bendable medical devices into a desired configuration and includes a first gripping tool and a moveable gripping tool. The first gripping tool can be either fixed with respect to a base or table for the robot or positioned at the end of robot arm. The moveable gripping tool is mounted to the end of a moveable robot arm having a proximal portion also mounted to the base. The robot preferably comprises a six axis bending robot, in which the distal end of the moveable arm can move relative to the fixed gripping tool about three translational axes and three rotational axes. The gripping tools preferably incorporate force sensors which are used to determine overbends needed to get the desired final shape of the archwire. The robot may also include a resistive heating system in which current flows through the wire while the wire is held in a bent condition to heat the wire and thereby retain the bent shape of the wire. A magazine for holding a plurality of straight archwires needing to be bent and a conveyor system for receiving the wires after the bending process is complete are also described. The robot bending system is able to form archwires with any required second and third order bends quickly and with high precision. As such, it is highly suitable for use in a precision appliance-manufacturing center manufacturing a large number of archwires (or other medical devices or appliances) for a distributed base of clinics.

U.S. Pat. No. 9,901,705 describes an apparatus, system, and method for creating a curvature on a medical device during a medical procedure, for example, selecting a curvature from a curve database, customizing the curvature for a specific patient anatomy, and applying the curvature to the medical device during the medical procedure.

It is an object of the present technology to ameliorate at least some of the inconveniences present in the prior art.

SUMMARY

Embodiments of the present technology have been developed based on developers' appreciation of certain shortcomings associated with the existing systems for forming a desired bend in orthodontic appliances.

In particular, developers have noted a difficulty with accurately and reproducibly achieving the desired bend in the orthodontic appliance during the pre-shaping. The process of pre-shaping the archwires into the desired shape is also referred to in the art as "shape forming" or "shape setting". It has been noted that orthodontic appliance materials, such as wires made of shape memory alloys, have a spring-back effect when released from its grip during bend formation. This requires a compensation in the form of an over-bend applied to the wire during bending. In other words, the wire must be bent further than the required angle of the desired bend. This problem is confounded by the fact that the required over-bend varies from orthodontic appliance to orthodontic appliance, most likely due to differences in elastic properties from the shape memory alloy composition, manufacturing method and archwire dimensions. These manufacturing tolerances may exist within and between batches of the orthodontic appliance blanks as produced. Consider also that each orthodontic appliance blank that is provided for pre-shaping has itself undergone a number of prior processing steps each with its own manufacturing tolerances (composition, casting, shaping). Furthermore, the ability to assess whether the desired bend has been achieved is highly dependent on: (i) operator skill and judgement, if performed manually, (ii) calibration of bending apparatus and bend assessment apparatus, if performed automatically or semi-automatically.

One consequence of multiple attempts to achieve the desired bend in the orthodontic appliance is a degradation in certain material properties, and ultimately failure of the material through material fatigue. Another consequence is an increased time, and hence cost, to manufacture each orthodontic appliance. Consequences to the patient of applying an orthodontic appliance with an incorrect pre-form bend is incorrect alignment of their teeth with possible impact on jaw alignment and associated medical problems, increased discomfort, and longer treatment, resulting in a higher cost.

Broadly, developers have determined a method and a system of forming a desired bend angle, by determining an initial angle determined by a trained Machine Learning Algorithm (MLA), and a feedback loop based on a computer vision analysis of a resultant bend angle after applying the initial angle.

From one aspect, there is provided a method for forming a desired bend angle in an orthodontic appliance, the method being implemented by a processor of a computer system, the computer system executing a Machine Learning Algorithm, the computer system operatively coupled to a bending apparatus, the method comprising obtaining an indication of the desired bend angle in the orthodontic appliance; determining, by the MLA, an initial bend angle to be applied to the orthodontic appliance during bending in a gripped state of the orthodontic appliance for achieving the desired bend angle in the orthodontic appliance when the orthodontic appliance is in a free state; causing the bending apparatus to form a bend having the initial bend angle in the orthodontic appliance, by bending the orthodontic appliance in the gripped state; monitoring the bending of the orthodontic appliance in the gripped state through a computer vision analysis; in response to the computer vision analysis rendering an indication that the initial bend angle in the orthodontic appliance in the gripped state has been reached, causing the bending apparatus to release at least a portion of the orthodontic appliance so that the orthodontic appliance is in the free state, measuring a resultant angle of the bend through the computer vision analysis, when the orthodontic appliance is in the free state; selectively executing: in response to the resultant angle being within a predefined tolerance level of the desired bend angle, determining that the orthodontic appliance has reached the desired bend angle; and in response to the resultant angle being outside the predefined tolerance level of the desired bend angle, iteratively applying an adjusted bend angle to the orthodontic appliance in the gripped state until the desired bend angle is achieved as determined by the computer vision analysis in the free state. The method may further comprise feeding the adjusted bend angle to the MLA to be used for further retraining of the MLA.

In certain embodiments, the obtaining the indication of the desired bend angle in the orthodontic appliance comprises receiving the indication from an operator of the computer system. In certain embodiments, the obtaining the indication of the desired bend angle in the orthodontic appliance comprises calculating, by the computer system, the desired bend angle.

In certain embodiments, the method further comprises, prior to the obtaining the indication of the desired bend angle: executing a training process for the MLA. The training process may include providing a feedback loop based on the computer vision analysis.

In certain embodiments, the training process comprises providing at least one training set, the training set including an indication of a property of the orthodontic appliance and a target value representative of a desired bend; the property of the orthodontic appliance including at least one of: an elasticity property of a material from which the orthodontic appliance is formed, a thickness of the orthodontic appliance, a diameter of the orthodontic appliance, a composition of the material from which the orthodontic appliance is formed, and a manufacturing process of the orthodontic appliance.

In certain embodiments, the training process further comprises: executing a test bending to bend a test orthodontic appliance to the desired bend; calculating a variance parameter between an actual bend and the desired bend; and feeding back the variance parameter to the MLA for further retraining of the MLA.

In certain embodiments, the method further comprises iteratively executing the training process until the variance parameter is within a pre-determined acceptable error threshold.

In certain embodiments, the monitoring of the bending of the orthodontic appliance comprises: capturing a sequence of images of the bend as it is being formed during the bending; filtering the images to determine a contour of the orthodontic appliance; determining at least one elongate axis of the orthodontic appliance from the contour; and determining an angle between the at least one elongate axis of the orthodontic appliance and a reference axis, or between two elongate axes of the orthodontic appliance. In certain embodiments, two elongate (longitudinal) axes of the orthodontic appliance are derived from the contour; and an angle between the two longitudinal axes of the orthodontic appliance is determined.

In certain embodiments, the reference axis is determined by projecting a virtual axis onto, and aligned with, the image of the orthodontic appliance before causing the bending apparatus to form the bend in the orthodontic appliance. In certain embodiments, the alignment of the virtual axis is maintained on an image of at least a portion of the orthodontic appliance during the bending process.

In certain embodiments, the filtering comprises one or more of image scaling, adjusting focus, and cancelling image noise. The filtering may further comprise transforming the format of the filtered images. In one embodiment, the format of the filtered images is transformed to HSV.

In certain embodiments, the monitoring of the bending of the orthodontic appliance comprises determining an angle of the bend being formed relative to a starting position or reference axis, the starting position comprising a virtual axis projected onto and aligned with the image of the orthodontic appliance before causing the bending apparatus to form the bend in the orthodontic appliance. The virtual axis can be a reference point. The virtual axis may be aligned with an elongate axis of the orthodontic appliance.

In certain embodiments, the monitoring the bending of the orthodontic appliance in the gripped state through the computer vision analysis comprises continuously monitoring the bending of the orthodontic appliance in the gripped state throughout an entire bending process. In certain embodiments, the monitoring the bending of the orthodontic appliance in the gripped state through the computer vision analysis comprises monitoring a bend angle of the orthodontic appliance in the gripped state throughout an entire bending process. In certain embodiments, the monitoring the bending of the orthodontic appliance in the gripped state through the computer vision analysis comprises acquiring a plurality of sequential image frames of the orthodontic appliance during the bending process at a frame acquisition rate related to a rate of bending. In certain embodiments, the frame acquisition rate is equal to or higher than about 70 frames per second, about 80 frames per second, about 90 frames per second, about 100 frames per second, about 150 frames per second, about 200 frames per second, about 250 frames per second, or about 300 frames per second. In certain embodiments, the frame acquisition rate is between about 70 to about 300 frames per second, about 100 to about 250 frames per second, or about 150 to about 200 frames per second.

From another aspect, there is provided a system for forming a desired bend angle in an orthodontic appliance, the system comprising a bending apparatus operatively coupled to a computer system; the computer system executing a Machine Learning Algorithm (MLA) and having a processor arranged to execute a method. The method comprises obtaining an indication of the desired bend angle in the orthodontic appliance; determining, by the MLA, an initial bend angle to be applied to the orthodontic appliance during bending in a gripped state of the orthodontic appliance for achieving the desired bend angle in the orthodontic appliance when the orthodontic appliance is in a free state; causing the bending apparatus to form a bend having the initial bend angle in the orthodontic appliance, by bending the orthodontic appliance in the gripped state; monitoring the bending of the orthodontic appliance in the gripped state through a computer vision analysis; in response to the computer vision analysis providing an indication that the initial bend angle in the orthodontic appliance in the gripped state has been reached, causing the bending apparatus to release at least a portion of the orthodontic appliance so that the orthodontic appliance is in the free state; measuring a resultant angle of the bend through the computer vision analysis, when the orthodontic appliance is in the free state; selectively executing: in response to the resultant angle being within a predefined tolerance level of the desired bend angle, determining that the orthodontic appliance has reached the desired bend angle; and in response to the resultant angle being outside the predefined tolerance level of the desired bend angle, iteratively applying an adjusted bend angle to the orthodontic appliance in the gripped state until the desired bend angle is achieved as determined by the computer vision analysis in the free state.

In certain embodiments, the system further comprises a computer vision system arranged to perform at least a portion of the computer vision analysis, the computer system and the computer vision system being operatively connected thereto.

From another aspect, there is provided a method for training a Machine Learning Algorithm (MLA), the MLA for determining, in use, a bend angle to be applied to an orthodontic appliance during bending in a gripped state for achieving a desired bend angle in the orthodontic appliance when in a free state, the method being implemented by a processor of a computer system, the computer system operatively coupled to a bending apparatus. The method comprises obtaining an indication of the desired bend angle in the orthodontic appliance; causing the bending apparatus to form a bend having an initial bend angle in the orthodontic appliance, by bending the orthodontic appliance in the gripped state; in response to receiving an indication that the initial bend angle in the orthodontic appliance in the gripped state has been reached, causing the bending apparatus to release at least a portion of the orthodontic appliance so that the orthodontic appliance is in the free state; obtaining a measure of a resultant angle of the bend, when the orthodontic appliance is in the free state; generating a training set for training the MLA, the training set including: an indication of a property of the orthodontic appliance and a target value representative of a desired bend; the property of the orthodontic appliance including at least one of: an elasticity property of a material from which the orthodontic appliance is formed, a thickness of the orthodontic appliance, a diameter of the orthodontic appliance, a composition of the orthodontic appliance, and a manufacturing method of the orthodontic appliance; the target value comprises the initial bend angle; and wherein the training set is configured to train the MLA to predict the initial bend angle based on the desired bend angle and the property of the orthodontic appliance.

In certain embodiments, the method further comprises calculating a difference parameter between the resultant angle of the bend and the initial bend angle and feeding the difference parameter as an indication of the prediction error.

In certain embodiments, the method further comprises iteratively repeating the method for training until the prediction error is within a pre-determined threshold.

In certain embodiments, the obtaining the measure of the resultant angle of the bend, when the orthodontic appliance is in the free state, comprises applying an optical feedback analysis. In certain embodiments, the obtaining the measure of the resultant angle of the bend can be performed in any other way, such as by force sensors and the like.

In certain embodiments, the optical feedback analysis comprises monitoring the bending of the orthodontic appliance in the gripped state through a computer vision analysis to determine when the initial bend angle in the orthodontic appliance in the gripped state has been reached; and measuring a resultant angle of the bend through the computer vision analysis, when the orthodontic appliance is in the free state; selectively executing: in response to the resultant angle being within a predefined tolerance level of the desired bend angle, determining that the orthodontic appliance has reached the desired bend angle; and in response to the resultant angle being outside the predefined tolerance level of the desired bend angle, iteratively applying an adjusted bend angle to the orthodontic appliance in the gripped state until the desired bend angle is achieved as determined by the computer vision analysis in the free state.

From another aspect, there is provided a system for training a Machine Learning Algorithm (MLA), the MLA for determining, in use, a bend angle to be applied to an orthodontic appliance during bending in a gripped state for achieving a desired bend angle in the orthodontic appliance when in a free state, the system comprising a computer system operatively coupled to a bending apparatus, the computer system having a processor arranged to execute a method. The method comprises: obtaining an indication of the desired bend angle in the orthodontic appliance; causing the bending apparatus to form a bend having an initial bend angle in the orthodontic appliance, by bending the orthodontic appliance in the gripped state; in response to receiving an indication that the initial bend angle in the orthodontic appliance in the gripped state has been reached, causing the bending apparatus to release at least a portion of the orthodontic appliance so that the orthodontic appliance is in the free state; obtaining a measure of a resultant angle of the bend, when the orthodontic appliance is in the free state; generating a training set for training the MLA, the training set including: an indication of a property of the orthodontic appliance and a target value representative of a desired bend, the property of the orthodontic appliance including at least one of: an elasticity property of a material from which the orthodontic appliance is formed, a thickness of the orthodontic appliance, a diameter of the orthodontic appliance, a composition of the orthodontic appliance, and a manufacturing method of the orthodontic appliance; the target value comprises the initial bend angle; and wherein the training set is configured to train the MLA to predict the initial bend angle based on the desired bend angle and the property of the orthodontic appliance.

In certain embodiments, any one or more of the method steps of (i) determining an initial bend angle to be applied, (ii) causing the bending apparatus to form a bend, (iii) monitoring the bending, (iv) rendering an indication that the initial bend angle has been reached, (v) measuring a resultant angle, (vi) determining that the resultant angle is within a predefined tolerance, (vii) determining that the resultant angle is not within a predefined tolerance and applying an adjusted angle, are performed in real-time. In certain embodiments, any one or more of these method steps are performed automatically without user intervention.

In certain embodiments, any one or more of the method steps of (i) determining an initial bend angle to be applied, (ii) causing the bending apparatus to form a bend, (iii) monitoring the bending, (iv) obtaining a measure of a resultant angle, and (v) generating a training set, are performed in real-time. In certain embodiments, any one or more of these method steps are performed automatically without user intervention.

In certain embodiments, the desired bend is achieved in the orthodontic appliance in fewer iterations compared with systems of the prior art. In certain embodiments, the desired bend is achieved in the orthodontic appliance faster compared with systems of the prior art.

In certain embodiments, the initial bend, provided by the MLA, angle can be achieved in a single step. This can reduce the number of iterations required to achieve the desired bend.

From another aspect, there is provided a method for monitoring a formation of a bend in an orthodontic appliance, the method being implemented by a processor of a computer system operatively connected to a computer vision system, the method comprising:

capturing a sequence of image frames of the orthodontic appliance during a bending process, the orthodontic appliance having a first bend arm and a second bend arm;

for at least one of the image frames of the sequence of image frames:
  applying image processing steps to objects in the image frames to determine a contour of the imaged orthodontic appliance including a contour of at least a portion of the first bend arm and a contour of at least a portion of the second bend arm;
  deriving one or more of: an elongate axis of the first bend arm based on the contour of the first bend arm, and an elongate axis of the second bend arm based on the contour of the second bend arm;
  determining a bend angle of the orthodontic appliance based on:
    the elongate axis of the first bend arm and the elongate axis of the second bend arm, or
    the elongate axis of the first bend arm or the second bend arm, and a reference axis;
wherein the bend angle of the orthodontic appliance is monitored continuously during the bend process.

In certain embodiments, the sequence of image frames is captured at an acquisition rate of about 70 to about 300 frames per second.

In certain embodiments, the image frames have a magnification of about 50× to about 400×.

In certain embodiments, the computer vision system further comprises a background surface against which the orthodontic appliance is imaged, wherein the background surface comprises one or more of a chroma-key surface and a light-absorbing surface.

In certain embodiments, the reference axis is determined by projecting a virtual axis onto, and aligned with, the image of the orthodontic appliance before causing the bending apparatus to form the bend in the orthodontic appliance.

In certain embodiments, the method further comprises maintaining the alignment of the virtual axis on an image of at least a portion of the orthodontic appliance during the bending process.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

Certain aspects and embodiments of the present technology, are directed to methods and systems for forming a desired bend in an orthodontic appliance. Other aspects and embodiments of the present technology are directed to training a Machine Learning Algorithm (MLA) for determining, in use, a bend angle to be applied to an orthodontic appliance during bending in a gripped state for achieving a desired bend angle in the orthodontic appliance when in a free state. By "gripped state" is meant that the orthodontic appliance is restrained in the ability to move freely, such as during bending of the orthodontic appliance when the orthodontic appliance is gripped on either side of the bend. By "free state" is meant that the orthodontic appliance is not restrained in the ability to move freely, such as when at least one end of the orthodontic appliance is released.

Figure 1:
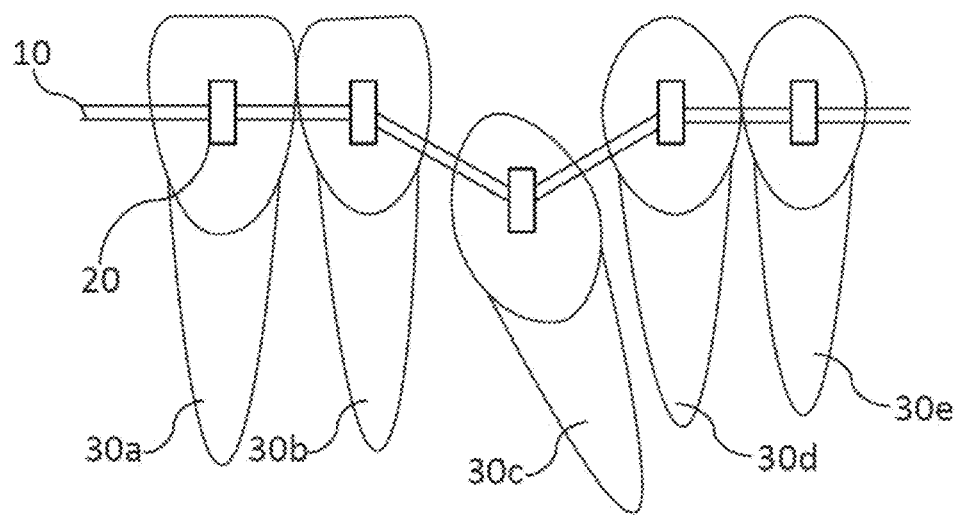
FIG. 1 is a schematic diagram of an orthodontic appliance attached to teeth with brackets, to which certain embodiments of the methods and systems of the present technology can be applied.

Referring initially to FIG. 1, there is shown an orthodontic appliance 10 to which aspects and embodiments of the present technology can be applied. In this embodiment, the orthodontic appliance 10 is an archwire 10 made of a shape memory alloy. The shape memory alloy is Nitonol™, but can also be any other shape memory alloy or material with elastic properties. Brackets 20 are provided on each tooth 30a, 30b, 30c, 30d, 30e, and the archwire 10 extends between, and is connected to, each of the brackets 20. As illustrated, the malocclusion is misalignment of the tooth 30c for which the treatment plan as illustrated is an upward movement to align the tooth 30c with neighbouring the teeth 30a, 30b, 30d, 30e.

Figure 2:
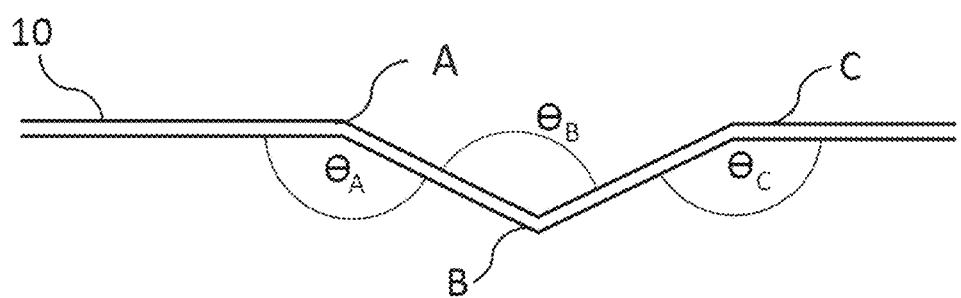
FIG. 2 is the orthodontic appliance of FIG. 1 showing bends formed in the orthodontic appliance according to certain embodiments of the methods and systems of the present technology.
Figure 3:
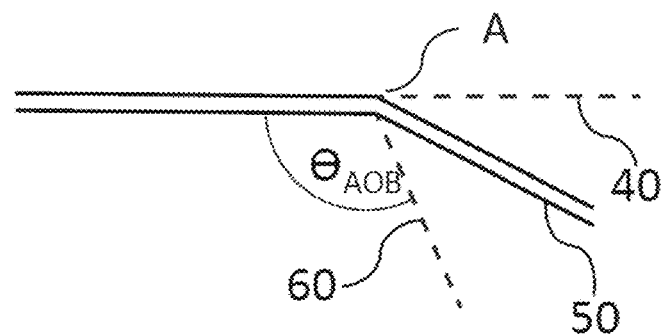
FIG. 3 is the orthodontic appliance of FIG. 2 showing different positions of the orthodontic appliance during formation of one of the bends according to certain embodiments of the methods and systems of the present technology.

As can be seen, the archwire 10 of FIG. 1 has three bends A, B and C with bend angles $\theta_A$, $\theta_B$ and $\theta_C$ respectively, shown in FIG. 2. FIG. 3 shows bend A of FIG. 2, including a starting position 40, a desired position 50 with the desired bend angle $\theta_A$, and an overbend position 60 having an overbend angle $\theta_{AOB}$ which must be applied during bend formation in order to achieve the desired bend angle $\theta_B$ due to an elastic property of the archwire 10.

It will be appreciated that in other embodiments, systems and methods of the present technology can be applied to different types, shapes, sizes and configurations of orthodontic appliances such as multi-strand wires, strips or retainers to adjust their configuration. Furthermore, the formed bends may comprise rounded corners or even loops. It will also be appreciated that the orthodontic appliance may be used for treating any type of teeth misalignment or malocclusion, including but not limited to closing gaps ("space closure"), creating/widening gaps, tooth rotation, tooth intrusion/extrusion, and translation, to name a few.

Figure 4:
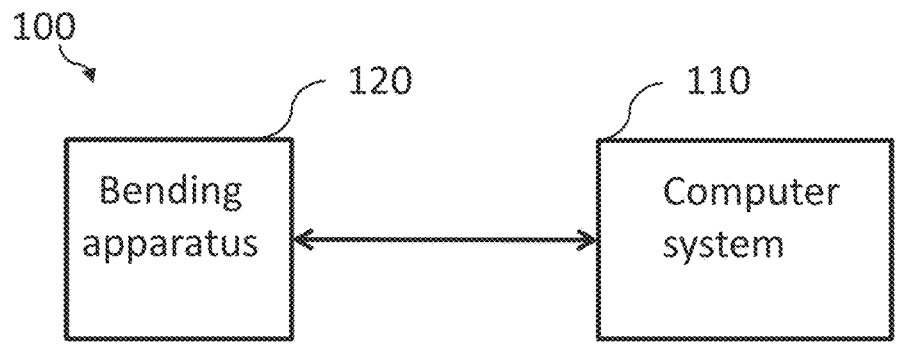
FIG. 4 is a system for forming bends in the orthodontic appliance, the system comprising a computer system and a bending apparatus, according to certain embodiments of the present technology.

Referring now to FIG. 4, there is shown one embodiment of a system 100 suitable for implementing non-limiting embodiments of the present technology. The system 100 will be described with reference to forming the desired bend angle $\theta_A$ in the bend A of the orthodontic appliance 10 of FIGS. 1-3.

It is to be expressly understood that the system 100 as depicted is merely an illustrative implementation of the present technology. Thus, the description thereof that follows is intended to be only a description of illustrative examples of the present technology. This description is not intended to define the scope or set forth the bounds of the present technology. In some cases, what are believed to be helpful examples of modifications to the system 100 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition it is to be understood that the system 100 may provide in certain instances simple implementations of the present technology, and that where such is the case they have been presented in this manner as an aid to understanding. As persons skilled in the art would understand, various implementations of the present technology may be of a greater complexity.

The system 100 of FIG. 4 comprises a computer system 110 operatively coupled to a bending apparatus 120. Broadly, responsive to instructions from the computer system 110, the bending apparatus 120 is configured to form a bend in the archwire 10 having an initial bend angle as determined in the gripped state. The bending apparatus is also arranged to grip or release the archwire 10 in order to allow transition between the gripped and free states. In these embodiments, monitoring of the bend of the archwire 10 and determination of the initial bend angle in the gripped state and a resultant bend angle in the free state can be performed by any means and this information provided to the computer system 110. The computer system 110 can, selectively execute, in response to the resultant angle being within a predefined tolerance level of an obtained desired bend angle (e.g. $\theta_A$) in the free state, determine that the archwire 10 has reached the desired bend angle; and in response to the resultant angle being outside the predefined tolerance level of the desired bend angle in the free state, iteratively apply an adjusted bend angle to the archwire 10 in the gripped state until the desired bend angle in the free state is achieved. Certain embodiments of the bending apparatus 120 will be described later with reference to FIG. 7.

Figure 5:
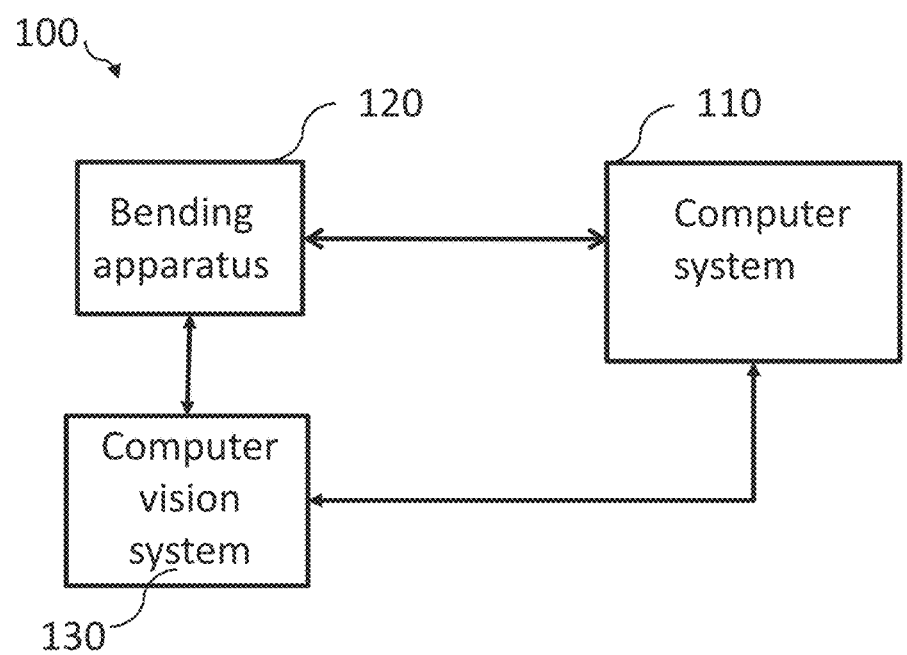
FIG. 5 is a system for forming bends in the orthodontic appliance, the system comprising a computer system, a bending apparatus and a computer vision system, according to certain embodiments of the present technology.

FIG. 5 illustrates another embodiment of the system 100 of FIG. 4, in which there is further provided a computer vision system 130 for providing a computer vision analysis of the bend. The computer vision system 130 is operatively connected to the computer system 110, and optionally connected to the bending apparatus 120. In certain embodiments, the computer vision system 130 is configured to monitor the bending of the archwire 10 in the gripped state for determining that the initial bend angle in the archwire 10 in the gripped state has been reached, and for measuring a resultant angle of the bend when the orthodontic appliance is in the free state. In certain embodiments, the computer vision system 130 is configured to continuously monitor the bending of the archwire 10 through an entire bending process. Certain embodiments of the computer vision system 130 and the computer vision analysis will be described later with reference to FIG. 8.

Figure 6:
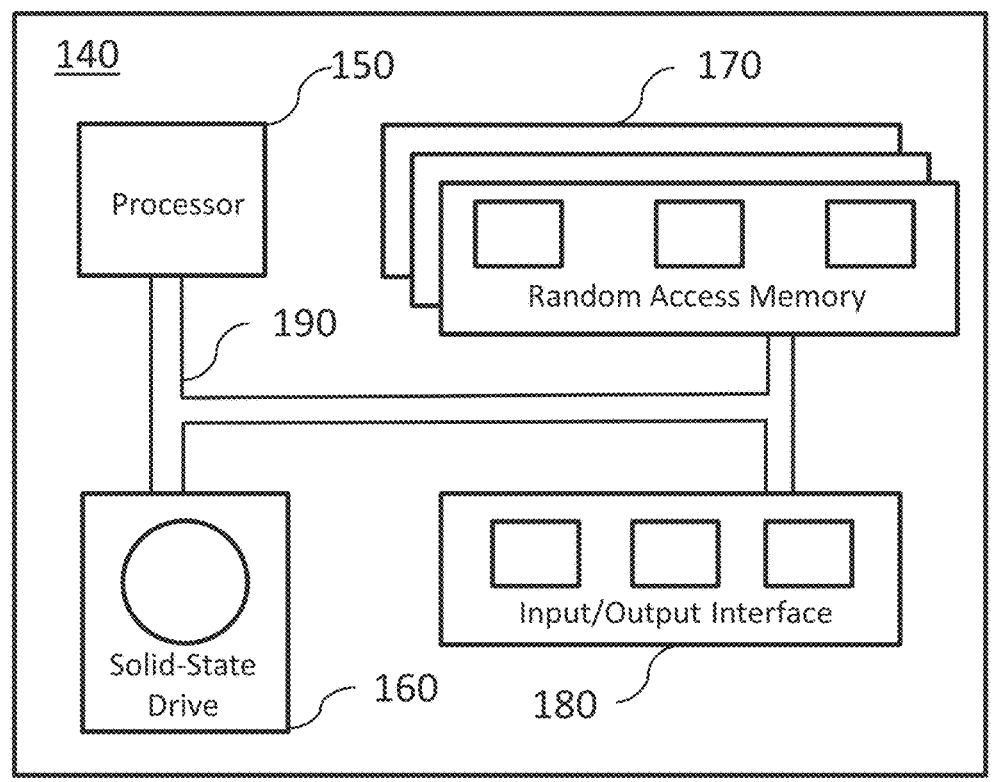
FIG. 6 is one embodiment of a computing environment of the computer system of FIG. 4 or FIG. 5 according to certain embodiments of the methods and systems of the present technology.

Turning first to the computer system 110, certain embodiments of the computer system 110 have a computer environment 140 as illustrated schematically in FIG. 6 and comprises various hardware components including one or more single or multi-core processors collectively represented by a processor 150, a solid-state drive 160, a random access memory 170 and an input/output interface 180. Communication between the various components of the computing environment 140 may be enabled by one or more internal and/or external buses 190 (e.g. a PCI bus, universal serial bus, IEEE 1394 "Firewire" bus, SCSI bus, Serial-ATA bus, ARINC bus, etc.), to which the various hardware components are electronically coupled.

The input/output interface 180 allows enabling networking capabilities such as wire or wireless access. As an example, the input/output interface 180 comprises a networking interface such as, but not limited to, a network port, a network socket, a network interface controller and the like. Multiple examples of how the networking interface may be implemented will become apparent to the person skilled in the art of the present technology. For example, but without being limiting, the networking interface 180 may implement specific physical layer and data link layer standard such as Ethernet, Fibre Channel, Wi-Fi or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 160 stores program instructions suitable for being loaded into the random access memory 170 and executed by the processor 150 for executing methods according to certain aspects and embodiments of the present technology. For example, the program instructions may be part of a library or an application.

In this embodiment, the computing environment 140 is implemented in a generic computer system which is a conventional computer (i.e. an "off the shelf" generic computer system). The generic computer system is a desktop computer/personal computer, but may also be any other type of electronic device such as, but not limited to, a laptop, a mobile device, a smart phone, a tablet device, or a server.

In other embodiments, the computing environment 140 is implemented in a device specifically dedicated to the implementation of the present technology. For example, the computing environment 140 is implemented in an electronic device such as, but not limited to, a desktop computer/personal computer, a laptop, a mobile device, a smart phone, a tablet device, a server, specifically designed for forming the desired bend angle in an orthodontic appliance. The electronic device may also be dedicated to operating other devices, such as the bending apparatus 120 and/or the computer vision system 130.

In some embodiments, the computing environment 140 is distributed amongst multiple systems, such as the bending apparatus 120, the computer vision system 130, and/or a server. In some embodiments, the computing environment 140 may be at least partially implemented in another system, as a sub-system for example. In some embodiments, the computer system 110 and the computing environment 140 may be geographically distributed.

As persons skilled in the art of the present technology may appreciate, multiple variations as to how the computing environment 140 is implemented may be envisioned without departing from the scope of the present technology.

Returning to the computer system 110 of FIGS. 4-6, the computer system 110 or the processor 150 implements, a machine learned algorithm (MLA) for determining, by the MLA, the initial bend angle to be applied to the orthodontic appliance during bending in the gripped state for achieving the desired bend angle in the free state.

The machine-learning algorithm, implemented by the computer system 100, may comprise, without being limitative, a non-linear regression, a linear regression, a logistic regression, a decision tree, a support vector machine, a naïve bayes, K-nearest neighbors, K-means, random forest, dimensionality reduction, neural network, gradient boosting and/or adaboost MLA.

In some embodiments, the MLA may be re-trained or further trained by the system 110 based on the data collected from the bending apparatus 120 and/or the computer vision system 130, as well as on various parameters relating to the archwire 10 such as composition, batch, manufacturer, diameter, width, thickness etc. In certain embodiments, the system 110 is also arranged to execute a training phase of the MLA. In other words, an output from the computer vision system 130 is fed back into the MLA for training or re-training.

Figure 7:
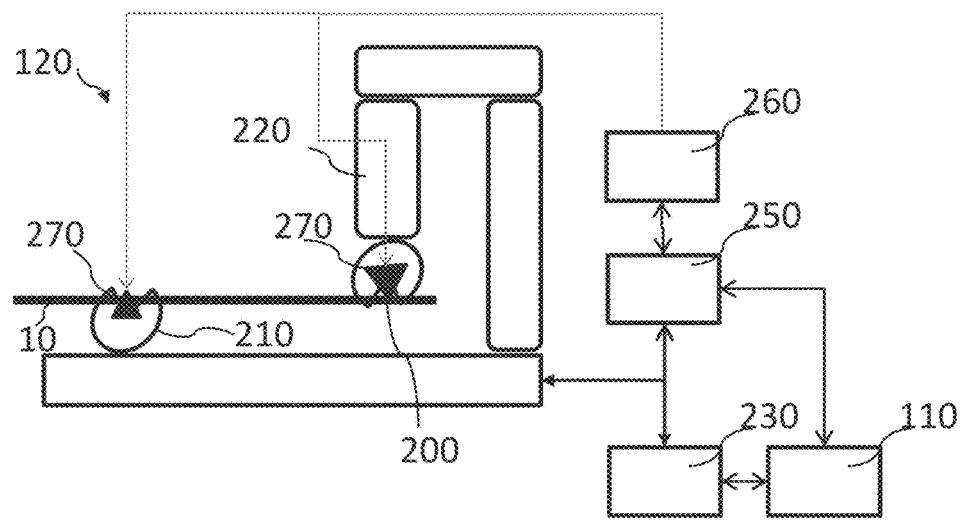
FIG. 7 is a schematic diagram of one embodiment of the bending apparatus of the system of FIG. 4 or FIG. 5 according to certain embodiments of methods and systems of the present technology.

Turning now to the bending apparatus 120, an embodiment of which is schematically illustrated in FIG. 7. As mentioned earlier, the bending apparatus 120 is arranged to form the bend in the archwire 10 based on instructions received from the computer system 110. The bending apparatus 120 comprises a first gripping member 200 and a second gripping member 210 configured to grip the archwire 10 along its length and move relative to each other whilst gripping the archwire 10 to form the bend in the archwire 10. The first gripping member 200 is attached to a robotic arm 220 having a plurality of axes of movement independent of the movement of the first gripping member 200. In this embodiment, the robotic arm 220 and the first gripping member 200 together provides six axes of movement. The bending apparatus 120 further comprises a robot control unit 230 for operatively controlling the movement of the first gripping member 200, the second gripping member 210 and the robotic arm 220. Bending of the archwire 10 is executed by relative movement of the first gripping member 200 to the second gripping member 210 whilst they are gripping the archwire 10. Each of the first and second gripping members 200, 210 have gripping surfaces (not shown) for gripping the archwire 10. The first and second gripping members 200, 210 can move between an open state, which releases the archwire 10, and a closed state, which grips the archwire 10. It will be appreciated that the archwire 10 can thus be transitioned from the gripped state to the free state through manipulation of the first and second gripping members 200, 210. The second gripping member 210 may be positionally fixed and immobile other than its operation between the closed and open states.

The robot control unit 230 is operatively connected to the computer system 110, such as to the processor 150, and can receive instructions from the computer system 110 regarding the movement and operation of the first gripping member 200, the second gripping member 210, and/or the robotic arm 220 to form the bend in the archwire 10. Information regarding the movement and operation of the first gripping member 200, the second gripping member 210, and/or the robotic arm 220 (e.g. co-ordinates) may be communicated between the robot control unit 230 and the computer system 110. This information may include any one or more of (i) a desired bend angle in the archwire 10 in the free state, (ii) the initial bend angle in the archwire 10 in the gripped state, (iii) an actual bend angle in the archwire 10 in the gripped state during bending, and (iv) the resultant bend angle of the archwire 10 in the free state. The actual bend angle in the archwire 10 in the gripped state during bending may also be expressed as a change in angle or a change in deflection. The robot control unit 230 may be operatively connected to the computer system 110 as a wired or wireless connection. The computer system 110 may be at least partially incorporated in the robot control unit 230.

Also provided is a heating system for heating the archwire 10 whilst under tension to form the pre-shape of the archwire 10. The heating system comprises a heating control unit 250 operatively connected to a power supply 260, and heating elements 270 for heating the archwire 10 through the first and second gripping members 200, 210. Heat may be generated electrically by electrical current and resistance in the circuit. Temperature sensor(s) are provided (not shown) for measuring the temperature of the archwire 10 and/or the heating elements 270. The heating control unit 250 is operatively connected to the computer system 110 or the robot control unit 230 and can receive instructions regarding operation of the heating of the archwire 10 from the computer system 110 or the robot control unit 230. Information regarding the temperature of the archwire 10 and/or the heating elements 270 is provided to the computer system 110 or the robot control unit 230 for determining an operation of the heating system. The operative connections between the heating control unit 250, the computer system 110 or the robot control unit 230 are wired or wireless.

Other configurations of the bending apparatus 120 are possible and included within the scope of the present technology. For example, the bending apparatus 120 may take the form of one or a combination of any of the bending apparatus as described in U.S. Pat. No. 6,612,143, U.S. Pat. No. 6,732,558, U.S. Pat. No. 6,755,064, U.S. Pat. No. 6,860,132, U.S. Pat. No. 7,076,980, U.S. Pat. No. 7,283,891, US2008/0154644 and US2010275668, the contents of which are incorporated herein by reference.

Figure 8:
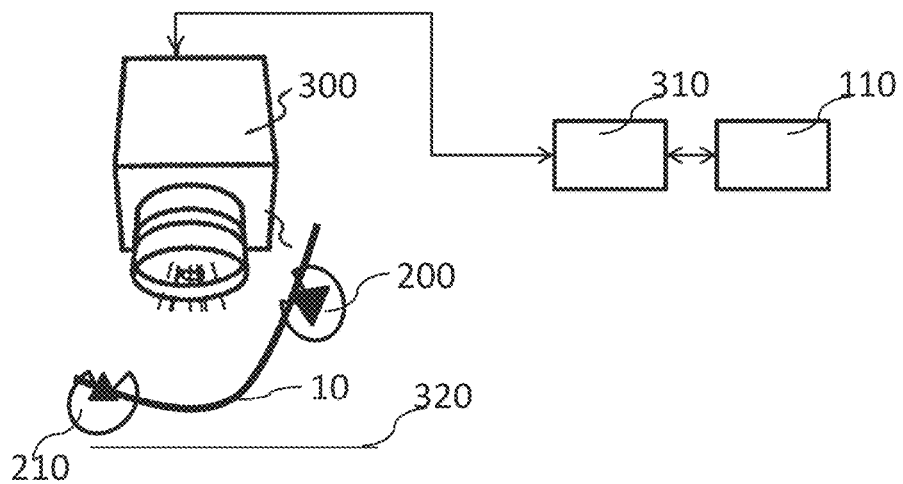
FIG. 8 is a schematic diagram of one embodiment of the computer vision system of the system of FIG. 4 or FIG. 5 according to certain embodiments of methods and systems of the present technology.

Turning now to FIG. 8 illustrating schematically certain embodiments of the computer vision system 130 of the system 100 of FIG. 5 for performing a computer vision analysis and for monitoring the bending of the archwire 10. The computer vision system 130 comprises a camera 300 for capturing images of the archwire 10 before, during and after bending, and a vision control unit 310 operatively connected to the computer system 110 for performing a computer vision analysis of the captured images.

In certain embodiments, the camera 300 is a microscope capable of capturing video images, as image frames, at magnifications of about 50× to about 400×. The microscope may use optical magnification or electronical (digital) magnification, which may also incorporate digital stabilization. In certain embodiments, the microscope may also use composite camera 300 with combined optical and digital magnification. The frame rate of image capture is proportionally related to the bending rate that can be used. In other words, the faster the frame rate, the faster the bending can be performed. In certain embodiments, the frame acquisition rate is 70 to 300 frames per second. In certain embodiments, the camera 300 is arranged to digitally capture images at a high frame rate, such as over 250 frames per second. In use, the camera 300 is arranged to focus on a segment of the archwire 10 which includes the bend or the area where the bend will be formed. Sequential image frames of this segment of the archwire 10 are captured during bending in real-time. The vision control unit 310 processes the captured images to obtain an angle of the bend, also in real-time, and relays the output of the image processing to the computer system 100.

In certain embodiments, the computer vision system 130 includes a background 320 that is positioned facing the camera 300 and behind the archwire 10 for providing a contrast of the archwire 10 against the background for ease of image processing. In certain embodiments, the background 320 is a chroma key background or a light-absorbing background such as Vantablack™. In certain embodiments, the computer vision system 130 includes a support surface on which the archwire 10 is placed as well as the background 320. In certain embodiments, the support surface comprises a chroma key surface, and the background comprises a light-absorbing surface.

The vision control unit 310 comprises a processor (not shown) for carrying out the computer vision analysis of the captured images to monitor a bend angle, and one or more databases (not shown) for storing the captured images and/or the processed images. The computer vision analysis can be performed on each frame, or on sampled frames of the sequence of frames. During a monitoring phase, the angle of the bend of the archwire 10 is determined as a function of time. The bend angle may be determined continuously during the bending process by continuous monitoring of the bend angle during the bending process. The determined angle may be an average based on closely-timed clusters of captured image frames of the imaged archwire segment.

The computer vision analysis comprises determining a contour of the imaged segment of the archwire 10. Based on the determined contour of the archwire 10, the computer vision analysis can derive one or more elongate axes of the determined contour, the contour corresponding to the imaged archwire 10 segment. For clarity, the imaged archwire 10 segment may include a bend and two bend arms, each of the bend arms having its own elongate axis. The angle of the bend can then be determined based on the elongate axes of the bend arms, in a manner that will be described later.

The contour of the imaged segment of the archwire 10 is determined using image processing or filtering steps. The image processing steps are selected from one or more of image pre-processing, image enhancement, image segmentation, image compression, image restoration, image representation, image recognition, image labelling, image format conversion and the like. Image pre-processing includes scaling (e.g. sizing, cropping). Image enhancement includes functions such as focus adjustment, and image noise cancellation (e.g. erosion). The processor is also configured to change formats of the captured images, such as to a HSV format (Hue, Saturation, Value), which allows separation of colour components from intensity for ease of certain image processing steps.

Figure 9:
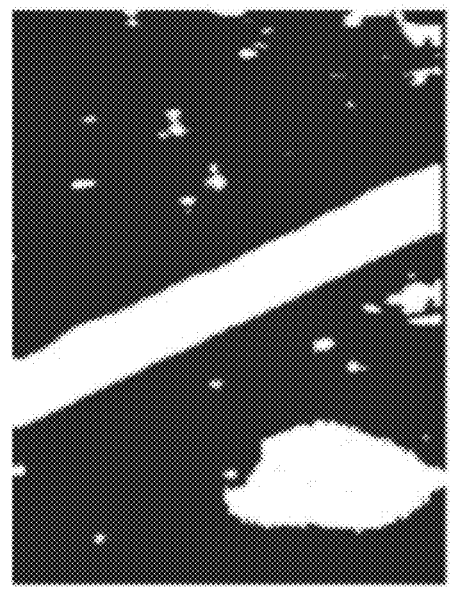
FIG. 9 is an example of an image of the orthodontic appliance captured by the computer vision system of FIG. 8 before image processing.

FIG. 9 depicts an example of a captured image frame of an imaged archwire 10 segment using the embodiment of the computer vision system 130 of FIG. 8. In this embodiment, the image processing steps include scaling and optionally sharpening of blurs, transformation of the image to HSV format, determining a lightness channel of the image, and image noise cancelation.

In certain embodiments, the image noise cancellation comprises removing smaller objects on the image using an erosion function. Relatively larger objects on the image are ignored based on a determined area of the object relative to its length, based on the fact that the imaged archwire 10 segments have an elongate form with larger areas. A further filtering can be performed based on a roundness of the object, with rounder objects being ignored. A time-based approximation can then be performed to reduce light noises (e.g. lens flares).

Figure 10:
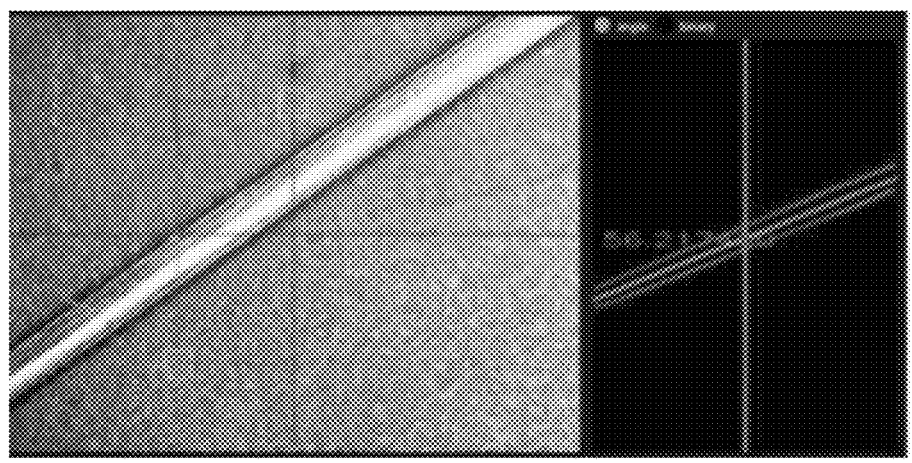
FIG. 10 is the image of the orthodontic appliance of FIG. 9 after image processing.

Referring back to determination of the angle of the bend from the imaged archwire 10, the bent archwire 10 has two bend arms, one on either side of the bend, and each having its own elongate axis. In certain embodiments, the angle of the bend comprises an angle between the respective elongate axes of the bend arms of the archwire 10. In other embodiments, one of the bend arms of the archwire 10 may be used as a reference axis for the bend angle determination. In this case, the reference axis may be established before the bending process is initiated, in a set-up phase, by projecting a virtual reference axis onto the image of the archwire 10. During bending, the virtual reference axis is maintained in alignment with one of the bend arms of the archwire 10 during the bending process. The angle of the bend is then determined as the angle between the virtual reference axis and the elongate axis of the other bend arm. In certain embodiments, the reference axis is the starting position 40 shown in FIG. 3. FIG. 10 shows a filtered image of the archwire 10 segment on the left, and a determined angle of the archwire 10 segment on the right.

The set-up phase may include a calibration step for normalizing variations in orientation between the camera 300 and the archwire 10 segment being imaged (this orientation may differ between different monitoring/bending tests). The calibration step comprises detecting an angle between a line of vision of the camera 300 and the archwire 10 segment being imaged, and normalizing this angle with a reference angle.

The bend angle of the archwire 10 in the free state is measured in a similar manner as described above. Specifically, once the bending apparatus 120 has released one of the gripping members 200, 210, images of the segment of the archwire 10 including the bend are captured, and processed as described above to determine the free state bend angle.

In other embodiments, the computer vision system 130 has a different configuration than the one described in relation to FIGS. 8-10. For example, the camera 300, or the image processing steps may differ. In certain embodiments, instead of a computer vision system 130, any other device or system for continuously monitoring the bending of the archwire 10 may be provided, such as strain gauges.

In some embodiments, the computer system 110 is connectable to the bending apparatus 120, and/or the computer vision system 130 via a communication network. In some embodiments, the communication network is the Internet and/or an Intranet. Multiple embodiments of the communication network may be envisioned and will become apparent to the person skilled in the art of the present technology.

In some embodiments, the computer system 110 is connectable to the bending apparatus 120, and/or the computer vision system 130 via the processor 150. In some other embodiments, the computer system 110 may be directly connected to the bending apparatus 120, and/or the computer vision system 130. In some alternative embodiments, the computer system 110 or the computing environment 140 is implemented, at least partially, on the bending apparatus 120, and/or the computer vision system 130. In yet some alternative embodiments, the computer system 110 may be hosted, at least partially, on a server. In some alternative embodiments, the system may be partially or totally virtualized through a cloud architecture.

Figure 11:
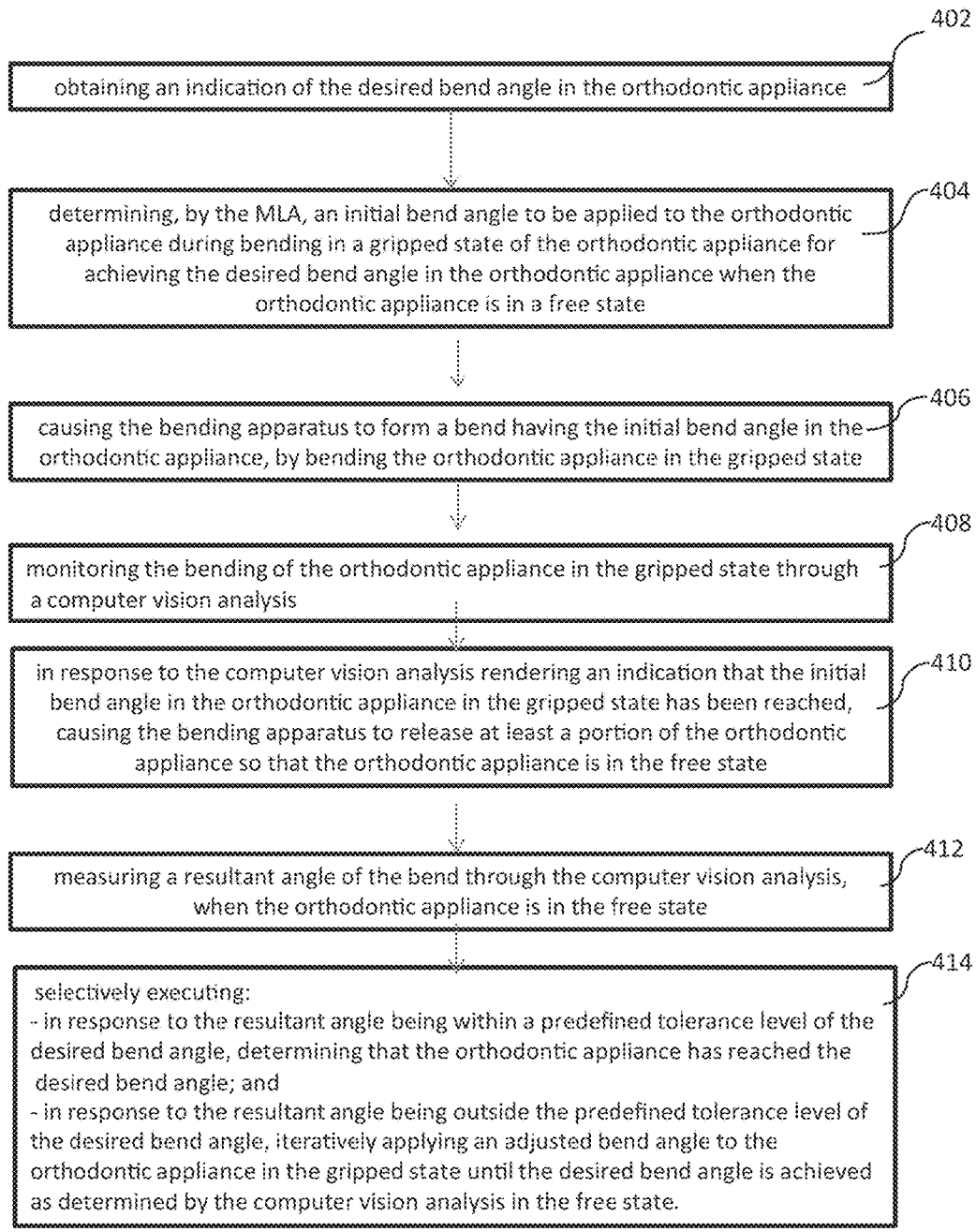
FIG. 11 is a diagram of a method for forming bends in the orthodontic appliance executed by the computer system of FIG. 4 or FIG. 5, in accordance with certain embodiments of the present technology.
Figure 12:
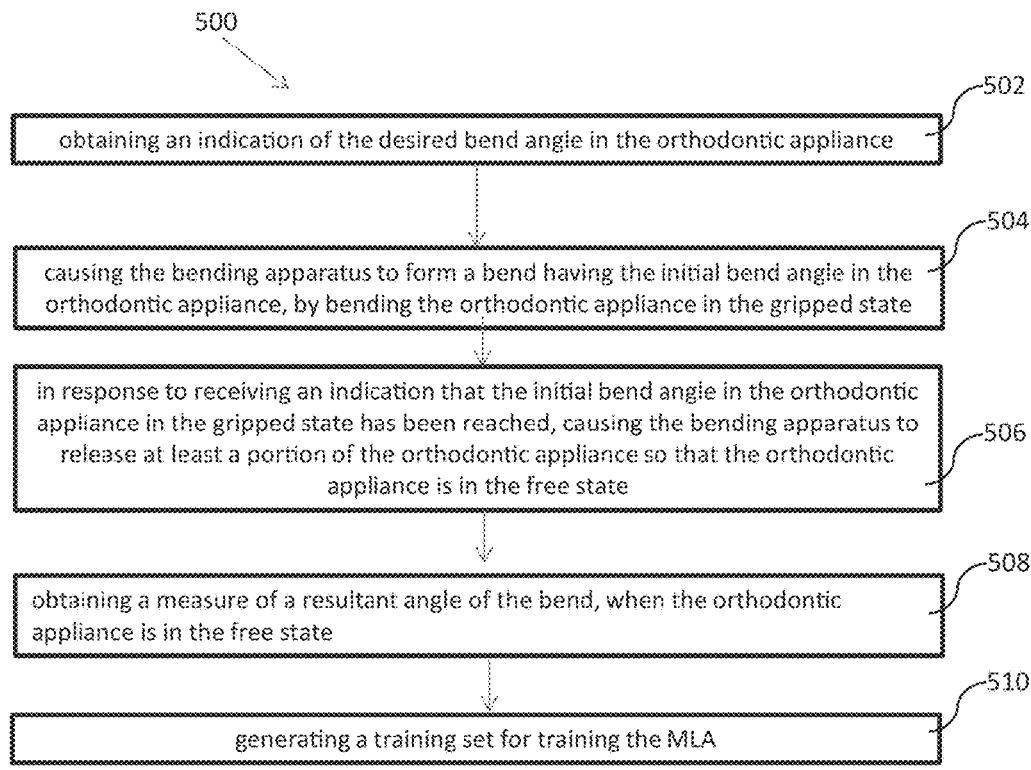
FIG. 12 is a diagram of a method for training a Machine Learning Algorithm executed by the computer system of FIG. 4 or FIG. 5, in accordance with certain embodiments of the present technology.

With reference now to FIG. 11, in certain embodiments the computer system 110 is configured to execute a method 400 for forming the desired bend angle in the archwire 10.

The method 400 will now be described in further detail below.

Step 402: Obtaining an Indication of the Desired Bend Angle in the Orthodontic Appliance The method begins at step 402 with the computer system 110 obtaining an indication of the desired bend angle in the orthodontic appliance (e.g. the archwire 10). In the embodiment of FIG. 2, the desired bend angle of bend A is the bend angle $\theta_A$ in the position 50. The desired bend angle is when the archwire is in the free state.

In certain embodiments, the desired bend angle is based on a treatment plan determined by a clinician, such as an orthodontist or a dentist. The desired bend angle can be determined by any method such as a manual determination or a computer model-based determination.

In certain embodiments, the obtaining the indication of the desired bend angle in the orthodontic appliance comprises receiving the indication from an operator of the computer system, such as through a user interface.

In other embodiments, the obtaining the indication of the desired bend angle in the orthodontic appliance comprises calculating, by the computer system 110 or another computer system, the desired bend angle.

For archwires 10 having a plurality of bends, such as the archwire 10 of FIGS. 1-3, the desired bend angle can be relative to a position of an adjacent portion of the archwire 10 as illustrated in FIG. 2. Alternatively, each desired bend angle can be determined based on a baseline starting position.

Step 404: Determining, by the MLA, an Initial Bend Angle to be Applied to the Orthodontic Appliance During Bending in a Gripped State of the Orthodontic Appliance for Achieving the Desired Bend Angle in the Orthodontic Appliance when the Orthodontic Appliance is in a Free State At step 404, the computer system 110 causes execution of the MLA to determine the initial bend angle to be applied to the orthodontic appliance, e.g. the archwire 10, in the gripped state, so that the desired bend angle in the free state can be achieved. In the example of FIG. 3, the initial bend angle is an over-bend angle $\theta_{AOB}$ to take into account an elastic property of the archwire 10 which causes it to spring back to the desired bend angle in the free state.

Step 406: Causing the Bending Apparatus to Form a Bend Having the Initial Bend Angle in the Orthodontic Appliance, by Bending the Orthodontic Appliance in the Gripped State In certain embodiments, the bend is formed by the computer system 100 sending instructions to the bending apparatus 120 of FIG. 7, for example. The bending apparatus 120, on receiving instructions from the computer system 110, grips the archwire 10 using the first and second gripping members 200, 210, and causes the archwire 10 to bend by applying a relative movement of the first and second gripping members 200, 210.

Step 408: Monitoring the Bending of the Orthodontic Appliance in the Gripped State Through a Computer Vision Analysis In certain embodiments, the computer vision analysis is performed by the computer vision system 130.

Monitoring of the bending of the orthodontic appliance may comprise: capturing a sequence of images of the bend of the archwire 10 as it is being formed during the bending; filtering or processing the images to determine a contour of the orthodontic appliance; determining two elongate (longitudinal) axes of the orthodontic appliance from the contour; and determining an angle between the two longitudinal axes of the orthodontic appliance.

In certain embodiments, the filtering of the images comprises one or more of image scaling, adjusting focus, and cancelling image noise. The filtering may also comprise converting the captured images to HSV image format.

In certain embodiments, the monitoring of the bending of the orthodontic appliance comprises determining an angle of the bend being formed relative to a starting position or reference axis. In certain embodiments, the starting position comprises projecting a virtual axis onto the image of the wire before the bending process is initiated, and aligning the virtual axis with the elongate axis of the archwire 10 before causing the bending apparatus to form the bend.

In certain embodiments, the monitoring the bending of the orthodontic appliance in the gripped state through the computer vision analysis comprises continuously monitoring the bending of the orthodontic appliance in the gripped state throughout an entire bending process. The monitoring can be in real-time.

Step 410: In Response to the Computer Vision Analysis Rendering an Indication that the Initial Bend Angle in the Orthodontic Appliance in the Gripped State has been Reached, Causing the Bending Apparatus to Release at Least a Portion of the Orthodontic Appliance so that the Orthodontic Appliance is in the Free State In certain embodiments, a feedback loop based on the computer vision analysis provides an indication to the computer system 110 that the initial bend angle has been reached. The computer system 110 can then provide instructions to the bending apparatus 120 to stop the bending operation, and to release the archwire 10 so that a measurement of a resultant bend angle in the free state can be performed.

Step 412: Measuring a Resultant Angle of the Bend Through the Computer Vision Analysis, when the Orthodontic Appliance is in the Free State In certain embodiments, the resultant angle of the bend is performed by capturing at least one image of the formed bend; filtering the image to determine a contour of the orthodontic appliance; determining two elongate (longitudinal) axes of the orthodontic appliance from the contour; and determining an angle between the two longitudinal axes of the orthodontic appliance.

In other embodiments, only one longitudinal axis is determined and compared to the starting position with which a segment of the archwire which did not move during bending is aligned.

In certain embodiments, the filtering of the image comprises one or more of image scaling, adjusting focus, and cancelling image noise. The filtering can further comprise converting the captured images to HSV format.

Step 414: Selectively Executing: In Response to the Resultant Angle being within a Predefined Tolerance Level of the Desired Bend Angle, Determining that the Orthodontic Appliance has Reached the Desired Bend Angle; and in Response to the Resultant Angle being Outside the Predefined Tolerance Level of the Desired Bend Angle, Iteratively Applying an Adjusted Bend Angle to the Orthodontic Appliance in the Gripped State Until the Desired Bend Angle is Achieved as Determined by the Computer Vision Analysis in the Free State.

In certain embodiments, if it is determined that the desired bend angle has been achieved according to a predefined tolerance level, the method ends at step 414.

In certain embodiments, if it is determined that the resultant angle is outside of the predefined tolerance level, the method continues by applying an adjusted bend angle to the archwire 10. The adjusted bend angle may be determined by the MLA and have the effect of reducing or increasing the resultant angle depending on whether the resultant angle was above or below the desired bend angle.

As before, the bending of the archwire 10 in the gripped state through the computer vision analysis is monitored. When the computer vision analysis renders an indication that the adjusted bend angle in the gripped state has been reached, the computer system 100 causes the bending apparatus 120 to release at least a portion of the archwire 10 so that the archwire 10 is in the free state and the resultant angle in the free state can be measured. The computer vision analysis determines the resultant angle in the free state. The method ends if the resultant angle in the free state is within the predefined tolerance level of the desired bend angle. If not, the method continues by applying further iteration(s) of a further adjusted bend angle to the archwire 10 until the desired bend angle in the free state of the archwire 10 is achieved as determined by computer vision analysis.

In a further step, the method 400 may comprise feeding the adjusted bend angle or the further adjusted bend angle, together with their respective resultant angles in the free state to the MLA to be used for further retraining of the MLA.

In certain embodiments, the method 400 further comprises the computer system 110 executing a training process for the training of the MLA. The training process may occur before the method steps 402-414 listed above. The training process may include providing a feedback loop based on a computer vision analysis.

In certain embodiments, the training process comprises providing at least one training set, the training set including an indication of a property of the archwire 10 and a target value representative of a desired bend. The property of the archwire 10 may include at least one of: an elasticity property of a material from which the archwire 10 is formed, a thickness of the archwire 10, a diameter of the archwire 10, a composition of the archwire 10, and a manufacturing process of the archwire 10.

In certain embodiments, the training process further comprises: executing a test bending to bend a test archwire 10 to the desired bend; calculating a variance parameter between an actual bend and the desired bend; and feeding back the variance parameter to the MLA for further retraining of the MLA.

In certain embodiments, the training process further comprises iteratively executing the training process until the variance parameter is within a pre-determined acceptable error threshold.

According to another aspect of the present technology, there is also provided a method 500 for training a Machine Learning Algorithm (MLA), the MLA for determining, in use, a bend angle to be applied to an orthodontic appliance during bending in a gripped state for achieving a desired bend angle in the orthodontic appliance when in a free state. The method 500 is implemented by the computer system 110, such as the processor 150, the computer system 110 being operatively coupled to the bending apparatus 120. The method 500 commences at step 502.

Step 502: Obtaining an Indication of the Desired Bend Angle in the Orthodontic Appliance The method begins at step 502 with the computer system 110 obtaining an indication of the desired bend angle in the orthodontic appliance (e.g. the archwire 10). In the embodiment of FIG. 2, the desired bend angle of bend A is the bend angle $\theta_A$ in the position 50. The desired bend angle is when the archwire 10 is in the free state.

In certain embodiments, the desired bend angle is based on a treatment plan determined by a clinician, such as an orthodontist or a dentist. The desired bend angle can be determined by any method such as a manual determination or a computer model-based determination.

In certain embodiments, the obtaining the indication of the desired bend angle in the orthodontic appliance comprises receiving the indication from an operator of the computer system, such as through a user interface.

In other embodiments, the obtaining the indication of the desired bend angle in the orthodontic appliance comprises calculating, by the computer system 110 or another computer system, the desired bend angle.

For archwires 10 having a plurality of bends, such as the archwire 10 of FIGS. 1-3, the desired bend angle can be relative to a position of an adjacent portion of the archwire 10 as illustrated in FIG. 2. Alternatively, each desired bend angle can be determined based on a baseline starting position.

Step 504: Causing the Bending Apparatus to Form a Bend Having the Initial Bend Angle in the Orthodontic Appliance, by Bending the Orthodontic Appliance in the Gripped State In certain embodiments, the bend is formed by the computer system 100 sending instructions to the bending apparatus 120 of FIG. 7, for example. The bending apparatus 120, on receiving instructions from the computer system 110, grips the archwire 10 using the first and second gripping members 200, 210, and causes the archwire 10 to bend by applying a relative movement of the first and second gripping members 200, 210.

Step 506: In Response to the Computer Vision Analysis Rendering an Indication that the Initial Bend Angle in the Orthodontic Appliance in the Gripped State has been Reached, Causing the Bending Apparatus to Release at Least a Portion of the Orthodontic Appliance so that the Orthodontic Appliance is in the Free State In certain embodiments, a feedback loop based on the computer vision analysis provides an indication to the computer system 110 that the initial bend angle has been reached. The computer system 110 can then provide instructions to the bending apparatus 120 to stop the bending operation, and to release the archwire 10 so that a measurement of a resultant bend angle in the free state can be performed.

Step 508: Obtaining a Measure of a Resultant Angle of the Bend Through the Computer Vision Analysis, when the Orthodontic Appliance is in the Free State In certain embodiments, the obtaining the measure of the resultant angle of the bend, when the orthodontic appliance is in the free state, comprises applying an optical feedback analysis.

The optical feedback analysis comprises, in certain embodiments, monitoring the bending of the orthodontic appliance in the gripped state through a computer vision analysis to determine when the initial bend angle in the orthodontic appliance in the gripped state has been reached; and measuring a resultant angle of the bend through the computer vision analysis, when the orthodontic appliance is in the free state. The optical feedback analysis further comprises the computer system 110 selectively executing: in response to the resultant angle being within a predefined tolerance level of the desired bend angle, determining that the orthodontic appliance has reached the desired bend angle; and in response to the resultant angle being outside the predefined tolerance level of the desired bend angle, iteratively applying an adjusted bend angle to the orthodontic appliance in the gripped state until the desired bend angle is achieved as determined by the computer vision analysis in the free state.

In certain embodiments, the resultant angle of the bend is performed by capturing at least one image of the formed bend; filtering the image to determine a contour of the orthodontic appliance; determining two longitudinal axes of the orthodontic appliance from the contour; and determining an angle between the two longitudinal axes of the orthodontic appliance.

In other embodiments, only one longitudinal axis is determined and compared to a virtual starting position axis with which a segment of the archwire which did not move during bending is aligned.

In certain embodiments, the filtering of the image comprises one or more of image scaling, adjusting focus, and cancelling image noise. The filtering can further comprise converting the captured images to HSV format.

Step 510: Generating a Training Set for Training the MLA

In certain embodiments, the training set includes an indication of a property of the archwire 10 and a target value representative of a desired bend.

The property of the archwire 10 may include at least one of: an elasticity property of a material from which the archwire 10 is formed, a thickness of the archwire 10, a diameter of the archwire 10, a composition of the archwire 10, and a manufacturing method of the archwire 10. The target value may comprise the initial bend angle.

The training set is configured to train the MLA to predict the initial bend angle based on the desired bend angle and the property of the archwire 10.

In certain embodiments, the method 500 further comprises calculating a difference parameter between the resultant angle of the bend and the initial bend angle and feeding the difference parameter as an indication of the prediction error.

In certain embodiments, the method further comprises iteratively repeating the method for training until the prediction error is within a pre-determined threshold.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method for forming a desired bend angle in an orthodontic appliance, the method being implemented by a processor of a computer system, the computer system executing a Machine Learning Algorithm (MLA), the computer system operatively coupled to a bending apparatus, the method comprising:

obtaining an indication of the desired bend angle in the orthodontic appliance;

determining, by the MLA, an initial bend angle to be applied to the orthodontic appliance during bending in a gripped state of the orthodontic appliance for achieving the desired bend angle in the orthodontic appliance when the orthodontic appliance is in a free state;

causing the bending apparatus to form a bend having the initial bend angle in the orthodontic appliance, by bending the orthodontic appliance in the gripped state;

monitoring the bending of the orthodontic appliance in the gripped state through a computer vision analysis;

in response to the computer vision analysis rendering an indication that the initial bend angle in the orthodontic appliance in the gripped state has been reached, causing the bending apparatus to release at least a portion of the orthodontic appliance so that the orthodontic appliance is in the free state, measuring a resultant angle of the bend through the computer vision analysis, when the orthodontic appliance is in the free state;

selectively executing:
- in response to the resultant angle being within a predefined tolerance level of the desired bend angle, determining that the orthodontic appliance has reached the desired bend angle; and
- in response to the resultant angle being outside the predefined tolerance level of the desired bend angle, iteratively applying an adjusted bend angle to the orthodontic appliance in the gripped state until the desired bend angle is achieved as determined by the computer vision analysis in the free state.

2. The method of claim 1, wherein the obtaining the indication of the desired bend angle in the orthodontic appliance comprises receiving the indication from an operator of the computer system.

3. The method of claim 1, wherein the obtaining the indication of the desired bend angle in the orthodontic appliance comprises calculating, by the computer system, the desired bend angle.

4. The method of claim 1, wherein the method further comprises, prior to the obtaining the indication of the desired bend angle:
executing a training process for the MLA.

5. The method of claim 4, wherein the training process includes providing a feedback loop based on the computer vision analysis.

6. The method of claim 1, further comprising feeding the adjusted bend angle to the MLA to be used for further retraining of the MLA.

7. The method of claim 4, wherein the training process comprises providing at least one training set, the training set including an indication of a property of the orthodontic appliance and a target value representative of a desired bend; the property of the orthodontic appliance including at least one of:
an elasticity property of a material from which the orthodontic appliance is formed,
a thickness of the orthodontic appliance,
a diameter of the orthodontic appliance,
a composition of the material from which the orthodontic appliance is formed, and
a manufacturing process of the orthodontic appliance.

8. The method of claim 7, wherein the training process further comprises:
executing a test bending to bend a test orthodontic appliance to the desired bend;
calculating a variance parameter between an actual bend and the desired bend;
feeding back the variance parameter to the MLA for further retraining of the MLA.

9. The method of claim 8, further comprising iteratively executing the training process until the variance parameter is within a pre-determined acceptable error threshold.

10. The method of claim 1, wherein the monitoring of the bending of the orthodontic appliance comprises:
capturing a sequence of images of the bend as it is being formed during the bending;
filtering the images to determine a contour of the orthodontic appliance,
determining at least one elongate axis of the orthodontic appliance from the contour; and
determining an angle between the at least one elongate axis of the orthodontic appliance and a reference axis, or between two elongate axes of the orthodontic appliance.

11. The method of claim 10, wherein the reference axis is determined by projecting a virtual axis onto, and aligned with, the image of the orthodontic appliance before causing the bending apparatus to form the bend in the orthodontic appliance.

12. The method of claim 10, wherein the filtering comprising one or more of image scaling, adjusting focus, and cancelling image noise, the filtered images being of HSV image format.

13. The method of claim 1, wherein the monitoring the bending of the orthodontic appliance in the gripped state through the computer vision analysis comprises continuously monitoring the bending of the orthodontic appliance in the gripped state throughout an entire bending process.

14. A method for training a Machine Learning Algorithm (MLA), the MLA for determining, in use, a bend angle to be applied to an orthodontic appliance during bending in a gripped state for achieving a desired bend angle in the orthodontic appliance when in a free state, the method being implemented by a processor of a computer system, the computer system operatively coupled to a bending apparatus, the method comprising:
obtaining an indication of the desired bend angle in the orthodontic appliance;
causing the bending apparatus to form a bend having an initial bend angle in the orthodontic appliance, by bending the orthodontic appliance in the gripped state;
in response to receiving an indication that the initial bend angle in the orthodontic appliance in the gripped state has been reached, causing the bending apparatus to release at least a portion of the orthodontic appliance so that the orthodontic appliance is in the free state,
obtaining a measure of a resultant angle of the bend, when the orthodontic appliance is in the free state;
generating a training set for training the MLA, the training set including:
an indication of a property of the orthodontic appliance and a target value representative of a desired bend;
the property of the orthodontic appliance including at least one of: an elasticity property of a material from which the orthodontic appliance is formed, a thickness of the orthodontic appliance, a diameter of the orthodontic appliance, a composition of the orthodontic appliance, and a manufacturing method of the orthodontic appliance;
the target value comprises the initial bend angle;
and wherein the training set is configured to train the MLA to predict the initial bend angle based on the desired bend angle and the property of the orthodontic appliance.

15. The method of claim 14, wherein the method further comprises calculating a difference parameter between the resultant angle of the bend and the initial bend angle and feeding the difference parameter as an indication of the prediction error.

16. The method of claim 14, further comprising iteratively repeating the method for training until the prediction error is within a pre-determined threshold.

17. The method of claim 14, the obtaining the measure of the resultant angle of the bend, when the orthodontic appliance is in the free state, comprises applying an optical feedback analysis.

18. The method of claim 17, wherein the optical feedback analysis comprises:
   monitoring the bending of the orthodontic appliance in the gripped state through a computer vision analysis to determine when the initial bend angle in the orthodontic appliance in the gripped state has been reached; and
   measuring a resultant angle of the bend through the computer vision analysis, when the orthodontic appliance is in the free state;
   selectively executing:
      in response to the resultant angle being within a predefined tolerance level of the desired bend angle, determining that the orthodontic appliance has reached the desired bend angle; and
      in response to the resultant angle being outside the predefined tolerance level of the desired bend angle, iteratively applying an adjusted bend angle to the orthodontic appliance in the gripped state until the desired bend angle is achieved as determined by the computer vision analysis in the free state.

19. A method for monitoring a formation of a bend in an orthodontic appliance, the method being implemented by a processor of a computer system operatively connected to a computer vision system, the method comprising:
   capturing a sequence of image frames of the orthodontic appliance during a bending process, the orthodontic appliance having a first bend arm and a second bend arm;
   for at least one of the image frames of the sequence of image frames:
      applying image processing steps to objects in the image frames to determine a contour of the imaged orthodontic appliance including a contour of at least a portion of the first bend arm and a contour of at least a portion of the second bend arm;
      deriving one or more of: an elongate axis of the first bend arm based on the contour of the first bend arm, and an elongate axis of the second bend arm based on the contour of the second bend arm;
      determining a bend angle of the orthodontic appliance based on:
         the elongate axis of the first bend arm and the elongate axis of the second bend arm, or
         the elongate axis of the first bend arm or the second bend arm, and a reference axis;
   wherein the bend angle of the orthodontic appliance is monitored continuously during the bend process.

* * * * *